United States Patent [19]

Stubbs

[11] 4,362,722
[45] Dec. 7, 1982

[54] SYNERGISTIC TICKICIDAL COMPOSITIONS CONTAINING ORGANOPHOSPHORUS COMPOUNDS AND CYCLOPROPANE CARBOXYLATES

[75] Inventor: Vincent K. Stubbs, Caboolture, Australia

[73] Assignee: ICI Australia Limited, Melbourne, Australia

[21] Appl. No.: 148,586

[22] Filed: May 12, 1980

[30] Foreign Application Priority Data

May 11, 1979 [AU] Australia .................. PD8767

[51] Int. Cl.³ .............. A01N 57/12; A01N 57/14; A01N 57/16
[52] U.S. Cl. .................. 424/219; 424/222; 424/203; 424/200
[58] Field of Search ........... 424/200, 304, 222, 203

[56] References Cited
U.S. PATENT DOCUMENTS 3,835,176  9/1974  Matsuo et al. .................. 424/304
4,144,331  3/1979  Felton et al. .................. 424/304

OTHER PUBLICATIONS

Frear, D., *Pesticide Index*, 4th ed., College Science Publishers, 1969, pp. 75, 90, 122, 199, 217, 229, & 328.
United Kingdom P.A., 2000764A, Huff, 1-17-79.

*Primary Examiner*—John F. Terapane
*Assistant Examiner*—F. T. Moezie
*Attorney, Agent, or Firm*—Cushman, Darby & Cushman

[57] ABSTRACT

This invention concerns synergistic compositions useful in the control or eradication of Ixodid ticks comprising a cyclopropanecarboxylic acid ester of formula I

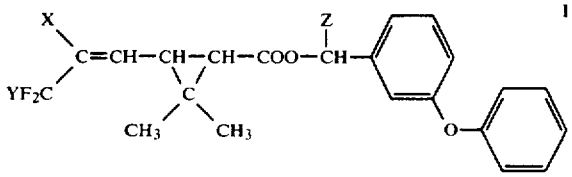

and at least one organophosphorus compound.

As a further feature the invention provides a process for the prevention of infestation by, or the control of infestations of, Ixodid ticks, and especially strains of the cattle tick *Boophilus microplus*.

10 Claims, No Drawings

SYNERGISTIC TICKICIDAL COMPOSITIONS CONTAINING ORGANOPHOSPHORUS COMPOUNDS AND CYCLOPROPANE CARBOXYLATES

This invention relates to a process for the control or eradication of Ixodid ticks and more particularly to a process for the treatment of animals to control or eradicate Ixodid ticks or to protect the animals from infestation by Ixodid ticks.

Ixodidae, or hard ticks, are responsible for the maintenance and propagation of a great many human and animal diseases throughout the world. The species of most economic importance include the *Boophilus* spp., *Rhipicephalus* spp., *Ixodes* spp., *Hyalomma* spp., *Ambylyomma* spp. and *Dermacentor* spp.

In Australia a problem of considerable economic importance is the control of ticks which infest cattle. Of these ticks the species *Boophilus microplus*, commonly known as the cattle tick, is responsible for the greatest economic losses in cattle production.

In the past "susceptible" or "non-resistant" strains of cattle tick have been controlled by means of sprays using as active ingredients certain chemicals such as arsenic, carbamates and chlorinated hydrocarbons. A typical "susceptible" strain is the "Yeerongpilly". Subsequently it was found that certain strains of cattle tick were emerging and becoming widespread in Australia and elsewhere and which were not affected by many of the broad-spectrum tickicides normally used for tick control. These strains are known as "resistant" strains of cattle tick and represent a serious problem to the cattle industry.

The "Yeerongpilly" strain is readily controlled with commercial tickicides such as carbaryl and DDT and is the strain used by all the authorities in Australia as the "susceptible" references stand against which the degree of resistance exhibited by emerging strains is measured. Table I lists the major resistant strains that have developed in *Boophilus microplus* in Australia. A major government enquiry established that eradication of cattle tick is not feasible because of geographical, technical and economic factors and the long term survival of the cattle industry in the northern half of Australia is critically dependent on the availability of effective tickicides.

When the early resistant strains emerged (Group I, Table I) they were readily controlled by a wide range of organophosphate (OP) tickicides, including those available commercially under the registered trade name of "Trithion" and "Delnav". Within a short period of time OP-resistant strains emerged and only the more potent OP tickicides were effective. Control of the most common strain of this type, "Ridgeland", typically involved OP's such as coumaphos, chloropyrifos, bromophosethyl and ethion. (Table II provides a concordance to the chemical name, common name and registered trade names of the main tickicides used against cattle ticks).

TABLE I

| Group | Strain | Date of Emergence |
|---|---|---|
| I | Arsenic - reistant | 1936 |
| | Dieldrin - resistant | 1953 |
| | DDT - resistant | 1955 |
| II | "Ridgeland" | 1963 |
| III | "Biarra" | 1966 |
| | "Mackay" | 1967 |
| IV | "Mt Alford" | 1971 |

TABLE I-continued

| Group | Strain | Date of Emergence |
|---|---|---|
| | "Gracemere" | 1971 |
| | "Silkwood" | 1971 |
| | "Bajool" | 1972 |
| | "Tully" | 1972 |
| | "Ingham" | 1972 |

Within a short period the virulent OP-resistant strain "Biarra" emerged and the number of commercially effective OP's was reduced to two, namely, bromophosethyl and chloropyriphos. Furthermore it was necessary to use these tickicides at twice the concentration previously employed in cattle dips to control the Group II strains thus adding to the cost of tick management. The risk of cattle exhibiting OP-poisoning symptoms also increased.

In 1971 a whole series of OP-resistant strains emerged of which the "Mt Alford" was the most difficult to control. In laboratory experiments the chloropyrifos application rate had to be increased a hundred-fold to control "Mt Alford" ticks and commercially such a rate was uneconomic and hazardous to cattle and dip operators.

The preferred method of treatment of cattle ticks in northern Australia uses large cattle "dips" which are troughs or baths, typically of concrete, containing the tickicidal composition. The cattle are herded into the dips and swim through the tickicidal composition. The dips need to have a minimum volume of about 10,000 liters so that the cattle are thoroughly emersed. The dips are "topped up" with water and tickicide periodically to replenish the material removed from the dip by the cattle, and to replace active tickicide lost through decomposition. The dips are maintained by this procedure as long as possible, sometimes for years, since emptying and cleaning is unpleasant and involves the loss of the expensive tickicide component. Stability of tickicides under such long term storage in contact with animal excreta and open to climatic conditions is thus a prime requirement.

Since the appearance of "Mt Alford" there are no longer any commercially available OP's with the necessary efficacy against the ticks and having the required dip storage stability. OP's have therefore been replaced in "Mt Alford"-infested areas with newer types of tickicides, such as the amidines. Unfortunately some of the amidines have limited stability in dips and require tedious management involving analysis and stabilization procedures. Furthermore, amidine-resistant strains are already in evidence.

Synthetic pyrethroid insecticides have been considered for use as tickicides but have the disadvantage of high manufacturing cost. In addition some are unstable to dip conditions or strong sunlight or both. No synthetic pyrethroid has yet been commercially developed in Australia despite the urgent need for new and better tickicides.

In Australian Patent Application No. 32,621/78 there are described cyclopropane carboxylates which are useful in the control of insect pests and other invertebrate pests such as, for example, acarina pests. Particularly useful pesticidal compounds which are described are the 3-phenoxybenzyl and α-cyano-3-phenoxybenzyl esters of 3-[2-halo(or trifluoromethyl)-3,3,3-trihaloprop-1-en-1-yl]-2,2-dimethylcyclopropane carboxylic acid in their various geometric and stereoisomeric forms which may be represented by the formula:

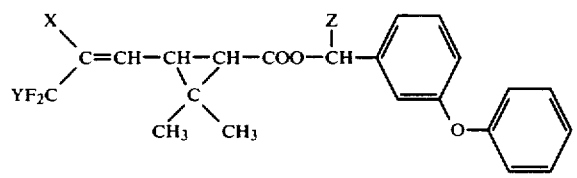

wherein X is fluoro, chloro, bromo or WF₂C and W and Y are independently hydrogen, chloro or fluoro and Z is hydrogen or cyano.

Australian Patent Application No. 32,621/78 also teaches that cyclopropane carboxylate derivatives disclosed in that application are effective in combatting both susceptible and resistant strains of ixodid ticks such as *Boophilus* spp., *Ixodid* spp., *Ambylomma* spp., *Rhipicephalus* spp. and *Dermaceutor* spp.

We have now found that the efficacy of the preferred compounds disclosed in Australia Patent Application No. 32,621/78 against Ixodid ticks may be significantly enhanced by the use of said compounds in combination with organophosphorus compounds. Furthermore, we have found that the enhanced efficacy cannot be explained in terms of the combined additive tickicidal efficacy of the components but results from synergism. For a given level of control of cattle ticks the quantity of cyclopropane carboxylate derivative required can be reduced with a consequent saving in cost.

Accordingly the invention provides a composition for use in combatting Ixodid ticks which composition contains as a first component at least one isomer of a cyclopropanecarboxylic acid ester of Formula I

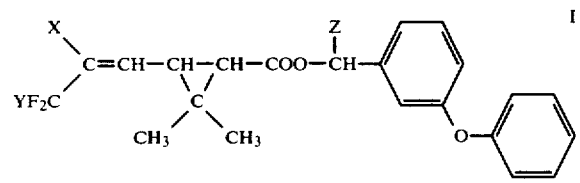

wherein X is chosen from fluorine, chlorine, bromine and the group WF₂C in which W is chosen from hydrogen, fluorine and chlorine, Y is chosen from hydrogen, fluorine and chlorine, and Z is hydrogen or cyano; and as a second component at least one organophosphorus compound.

Preferred cyclopropanecarboxylic acid esters for use in the compositions of the invention include the following compounds in their various geometric and stereoisomeric forms:

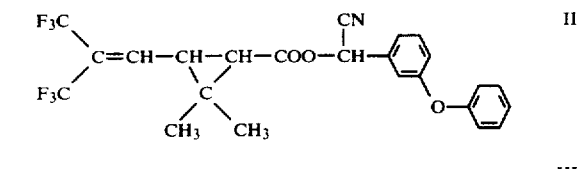

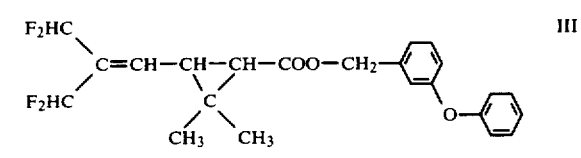

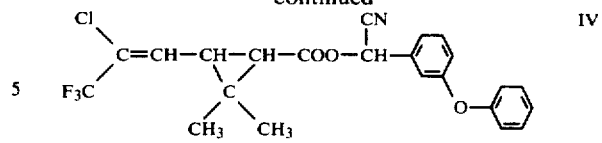

and mixtures thereof.

The nature of the organophosphorus compound may be varied widely. For example suitable organophosphorus compounds include aliphatic compounds, aromatic compounds or compounds comprising heterocyclic rings. Typical classes of organophosphorus compounds suitable for use in the invention include organophosphates (which may be represented by the chemical known by the common name of chlorofenvinphos); phosphorus-bearing phenyl esters (bromophosethyl), which optionally may contain sulphur-bearing substituents (fenthion); phosphorus-bearing derivatives of thioethers (ethion); or phosphorylated heterocyclic ring compounds having at least one oxygen or nitrogen atom in the heterocyclic ring (coumaphos, diazinon). Particularly useful organophosphorus compounds include those wherein the phosphorus-bearing radical is a phosphate, a phosphorothioate, a phosphorodithioate, or a di(phosphorodithioate). Examples of typical organophosphorus compounds suitable for use in the invention are set out in Table II below. In referring to these compounds they are described as set out in the well known and authorative dictionary of pesticides and chemical pollutants entitled "Nanogen Index", published by Nanogens International of Freedom, USA 1975 edition and having a Library of Congress Catalog Card Number 75-14751. For ease of description the compounds are also referred to by their common name, by a designation (indicated by an invented word in inverted commas) which is a registered trade mark in some countries and, in some instances, by an abbreviation used hereinafter in the examples which illustrate the invention.

Preferred organophosphorus compounds for use in the composition of the invention include O-(4-bromo-2,5-dichlorophenyl)O,O-diethylphosphorothioate, commonly referred to as bromophos-ethyl, and O,O,O'-,O-tetraethyl-S,S'-methylenedi(phosphorodithioate), commonly referred to as ethion.

TABLE II

| Chemical Name | Common Name | Invented Word | Abbreviation |
|---|---|---|---|
| Mixed cis/trans isomers of 2-chloro-1-(2,4-dichlorophenyl)vinyl diethyl phosphate | chlorfenvinphos | "Birlane" | CHLOR |
| O—(4-bromo-2,5-dichlorophenyl) O,O—diethyl phosphorothioate | bromophos-ethyl | "Nexagan" | — |
| O,O—diethyl O—3,5,6-trichloro-2-pyridyl-phosphorothioate | chloropyrifos | "Dursban" | — |
| O,O-diethyl O—(3-chloro-4-methyl-7-coumarinyl) phosphorothioate | coumaphos | "Asuntol" | ASUN |
| O,O—diethyl O—(2-isopropyl-6-methyl-4-pyrimidinyl) phosphorothioate | diazinon | "Basudin" | DIAZ |
| O,O—dimethyl O—p-(dimethylsulphamoyl) phenyl phosphorothioate | famphur | "Famophos" | FAMP |

TABLE II-continued

| Chemical Name | Common Name | Invented Word | Abbreviation |
|---|---|---|---|
| O,O—dimethyl O—(3-methyl-4-methylthio-phenyl) phosphorothioate | fenthion | "Baycid" | FEN |
| O,O—diethyl O—(2-diethylamino-6-methylpyrimidin-4-yl) phosphorothioate | pirimiphos-ethyl | "Primicid" "Solgard" | — |
| O,O—dimethyl phthalimido methyl phosphorodithioate | phosmet | "Prolate" | PROL |
| O,O,O',O'—tetraethyl-S,S'—methylene di(phosphorodithioate | ethion | "Nialate" | — |
| S—[(p-chlorophenyl-thio)-methyl] O,O—diethyl phosphorodithioate | carbo-phenothion | "Trithion" | CARBO |
| S,S'—p-dioxan-2,3-diyl O,O,O',O'—tetraethyl-phosphorodithioate | dioxathion | "Delnav" | — |

The ratio of the components of the pesticidally active material in our compositions may be varied to suit the conditions under which the composition is to be used and also to provide an economic, effective composition dependent on the cost of the components and the extent of the synergism exhibited by the particular combination of compounds used in the composition. By synergism we mean the cooperative action of two or more agents in a composition in such a way that the total effect is greater than the sum of the individual effects taken individually. Suitable compositions include those having a weight ratio of the first component to the second component in a range from 5:1 to 1:100. At the present time the cost of the cyclopropanecarboxylic type components is more than the cost of an equal weight of the organophosphorus component and thus from an economic aspect it is desirable that the organophosphorus component comprise at least 25% of the pesticidal mixture in the compositions of the invention. Preferably therefore in such compositions the weight ratio of the first component to the second component lies in a range from 3:1 to 1:2.

The compositions of the invention are useful in the prevention of infestation by, or for the control of infestations of, Ixodid ticks on media such as buildings and pastures, and on animals such as horses, sheep, dogs and cattle.

Thus in a further embodiment the invention provides a process for the prevention of infestation by Ixodid ticks, or for the control or eradication of infestations of Ixodid ticks, which process comprises applying to the media to be protected, or to the infested media, an effective amount of a composition comprising as a first component at least one isomer of a cyclopropanecarboxylic acid ester of formula I as hereinbefore defined and as a second component at least one organophosphorus compound.

The compositions of the invention give high contact activity against various strains of the cattle tick *Boophilus microplus* in the adult, larval and intermediate stages, and both the "susceptible" and "resistant" strains may be controlled. This simultaneous efficacy against both the "susceptible" and "resistant" strains of *Boophilus microplus* is of considerable and increasing economic importance.

Accordingly in yet a further embodiment the invention provides a process for the control or eradication of the cattle tick *Boophilus microplus* which process comprises treating cattle infested with the cattle tick *Boophilus microplus* with a tickicidally effective amount of a composition comprising as a first component at least one isomer of a cyclopropanecarboxylic acid ester of formula I as hereinbefore defined and as a second component at least one organophosphorus compound.

The compositions of the invention preferably comprise an inert carrier to aid in the application of the active ingredients. The carrier may comprise solids in the form of dusting powders or granules or shaped polymeric materials through which the active ingredients are capable of migrating. Preferably the carrier is an aqueous liquid formulation.

The liquid formulations, which may be used as dips or sprays, are generally aqueous dispersions of emulsions containing the active ingredients in the presence of one or more wetting agents, dispersing agents, emulsifying agents or suspending agents. Emulsifiable solutions or suspensions of the active ingredients may be prepared by dissolving or suspending them in a solvent, or mixture of solvents, which is not harmful to the media to be treated, adding an emulsifier and/or wetting agent and optionally, adding some water. Suitable solvents are, for example, ethylene dichloride, isopropyl alcohol, propylene glycol, diacetone alcohol, toluene, xylenes, kerosene, cyclohexanone, methylnaphthalene and trichloroethylene.

Solid formulations, which may be used as dusting powders or granules, are generally compositions wherein the active ingredients are mixed with a solid diluent or carrier. Suitable solid diluents or carriers may be, for example, kaolinite (china clay), montmorillonite, attapulgite, talc, pumice, silica, calcium carbonate, gypsum, powdered magnesia, Fuller's earth, Hewitt's earth and diatomaceous earth.

Solid compositions may also be in the form of dispersible powders or grains comprising, in addition to the active ingredients, a wetting agent to facilitate the dispersion of the powder or grains in liquids. Such powders or grains may include fillers, suspending agents and the like. The compositions may also be in the form of aqueous pastes.

The compositions may also be in the form of capsules or microcapsules containing either the active ingredients themselves, or a composition containing the active ingredients and prepared by any of the known encapsulation or microencapsulation techniques.

By the inclusion of suitable additives, for example, for improving the distribution, adhesive power and resistance to rain on treated surfaces, the different compositions can be better adapted for the various uses for which they are intended.

Solid compositions may also be in the form of solid shaped articles comprising a mixture of the active ingredients and a polymeric material from which the active ingredients can migrate. Such shaped articles are of particular use when in the form of bands, collars, and especially ear- and tail-tags, for attachment to the animal to be treated. Suitable polymeric materials include, for example, the lower polyolefins, poly(vinyl chloride), poly(vinyl fluoride), poly(chlorotrifluoroethylene), polyurethanes, polycarbonate, polyesters including poly(ethylene terephthalate), poly(vinylidene chloride), poly(benzimidazole), ethylene-acrylic acid copolymer ionomers, cellulose acetate, regenerated cellulose film, polystyrene and etc. Alternatively solid compositions may be in the form of solid shaped articles comprising the active ingredients or a composition containing the active ingredients enclosed within a polymeric wall element through which the active ingredient can migrate. Suitable polymeric wall elements include the polymeric materials listed above and laminates of those polymeric materials.

The compositions which are to be used in the form of aqueous dispersions or emulsions are generally supplied in the form of a concentrate containing a high proportion of the active ingredients, the said concentrate to be diluted with water before use.

These concentrates are often required to withstand storage for prolonged periods and after such storage, to be capable of dilution with water in order to form aqueous preparations which remain homogeneous for a sufficient time to enable them to be applied by conventional spray equipment. The concentrates may conveniently contain from 0.1–85% by weight of the active ingredients and generally from 0.5–50% by weight of the active ingredients. When diluted to form aqueous preparations, such preparations may contain varying amounts of the active ingredients depending upon the purpose for which they are to be used, but an aqueous preparation containing between 0.0001% and 5.0% by weight of the active ingredients may be used.

Suitable dose rates of the active ingredient for the control of infestations of Ixodid tick are not narrowly critical and are dependent to some extent on the Ixodid tick being treated. Rates will also be related to the mode of application of the active ingredients, for example the rate will vary for each type of application such as dipping, spraying or dusting of the infested surface. As a general guide for the treatment of cattle infested by *Boophilus microplus*, dips containing up to 5% w/w of active ingredients are satisfactory for most degrees of severity of infestation by "resistant" strains of tick and adequate control may be effected in many instances where the concentration of active ingredients in a dip is in the range from 0.0005% to 1.0% w/w.

Liquid formulations, preferably concentrated liquid formulations, may also be applied to the media to be treated as a "pour-on" formulation. This technique is especially applicable to the treatment of animals such as cattle as the active ingredient is generally rapidly dispersed over the animal's body by tail and head movement.

It is to be understood that the tickicidal compositions used in the process of this invention may comprise, in addition to one or more compounds from the class of compounds described, one or more other compounds having biological activity.

The invention is now illustrated, but not limited, by the following Examples in which all parts are parts by weight unless otherwise indicated.

EXAMPLE 1

In this comparative Example a composition was prepared by the admixture of 25 parts of (±)-α-cyano-3-phenoxybenzyl (±)-cis/trans-3-(2-chloro-3,3,3-trifluoroprop-1-en-1-yl)-2,2-dimethylcyclopropane carboxylate (CPC-I), 45 parts of mineral oil available commercially under the designation of "Shell" 21, 6 parts of a composition comprising a blend of anionic and non-ionic surfactants and available commercially under the designation "Atlox" 3404F, 3 part of a non-ionic surfactant available commercially under the designation "Aromasol" H ("Shell", "Atlox", "Teric" and "Aromasol" are Trade Marks). Portions of the compositions so prepared were then diluted with water to provide dilute test compositions containing various amounts of the cyclopropane carboxylate as shown in Table I.

Twenty engorged adult female cattle ticks of the "resistant" Biarra strain of *Boophilus microplus* were supported on a mesh carrier and immersed in a dilute test composition briefly until they had reached drip point (5 seconds) and were then removed from the test composition. After 14 days the mortality of the adult ticks was assessed by determining the percentage of viable eggs laid. The results are shown in Table III wherein the tabulated concentration of the cyclopropane carboxylate is expressed in parts of the compound per million parts of the dilute test composition (ppm).

TABLE III

| Concentration of Cyclopropane Carboxylate (ppm) | % Mortality of Engorged Adult Female Ticks of the Biarra Strain |
|---|---|
| 200 | 98 |
| 100 | 73 |
| 50 | 47 |
| 25 | 31 |
| 12.5 | 17 |

EXAMPLES 2 AND 3

In these comparative Examples the general procedure outlined in Example 1 was repeated except that the dilute test compositions of the cyclopropane carboxylate CPC-I were replaced by compositions obtained by diluting the commercially available organophosphorus compositions Ethion and Bromophos-ethyl with water to provide dilute test compositions of the appropriate concentration. The results are shown in Table IV wherein the tabulated concentration of the organophosphorus compound is expressed in parts per million (ppm).

TABLE IV

| Example No | Organophosphorus Compound | Concentration ppm | Mortality Rate % |
|---|---|---|---|
| 2 | Ethion | 400 | 9 |
|   | Ethion | 200 | 0 |
|   | Ethion | 100 | 0 |
| 3 | Bromophos-ethyl | 400 | 10 |
|   | Bromophos-ethyl | 200 | 0 |
|   | Bromophos-ethyl | 100 | 0 |

EXAMPLES 4 AND 5

These Examples demonstrate tickicidal compositions of the invention having synergistic characteristics and comprising (±)-α-cyano-3-phenoxybenzyl (±)-cis/trans-3-(2-chloro-3,3,3-trifluoroprop-1-en-1-yl)-2,2-dimethylcyclopropane carboxylate and an organophosphorus compound. The general procedure outlined in Example 1 was repeated except that the dilute test compositions of the cyclopropane carboxylate were replaced by compositions containing a mixture of the cyclopropane carboxylate (CPC-I) and an organophosphorus compound (OP). The results and the concentration of the components in the test composition are shown in Table V wherein the expected percentage mortality was obtained from comparative Examples 1, 2 and 3.

TABLE V

| Example No | OP | Concentration (ppm) CPC-I | Concentration (ppm) OP | % Mortality Observed | % Mortality Expected |
|---|---|---|---|---|---|
| 4 | Ethion | 200 | 400 | 97 | 100 |
|  |  | 100 | 200 | 98 | 73 |
|  |  | 50 | 100 | 72 | 47 |
|  |  | 25 | 50 | 37 | 31 |
|  |  | 12.5 | 25 | 35 | 17 |
| 5 | Bromophos-ethyl | 200 | 400 | 100 | 100 |
|  |  | 100 | 200 | 95 | 73 |
|  |  | 50 | 100 | 86 | 47 |
|  |  | 25 | 50 | 53 | 31 |

EXAMPLES 6-13

The procedure of Examples 4 and 5 was repeated with (±)-α-cyano-3-phenoxybenzyl (±)-cis-3-(2-chloro-3,3,3-trifluoroprop-1-en-1-yl)-2,2-dimethylcyclopropane carboxylate (CPC-II) and the range of organophosphorus compounds listed in Tables VI and VII. The comparative examples with separate formulations of CPC-II and the organophosphorus compounds are included in those Tables and designated "controls". Separate control experiments were used for the two groups of experiments, Examples 6 and 7 (Table VI), Examples 8-13 (Table VII).

TABLE VI

| Example No | Cyclopropanecarboxylate, organophosphorus compound | Concentration ppm CPC-II | Concentration ppm OP | Mortality % Observed | Mortality % Expected |
|---|---|---|---|---|---|
| (control) | CPC-II | 200 | — | 97 | — |
|  |  | 100 | — | 55 | — |
|  |  | 50 | — | 17 | — |
|  |  | 25 | — | 0 | — |
| (control) | Ethion | — | 200 | 9 | — |
| (control) | Bromophos-ethyl | — | 200 | 5 | — |
| 6 | CPC-II/Ethion | 100 | 200 | 99 | 64 |
|  |  | 100 | 100 | 95 | 55 |
|  |  | 100 | 25 | 82 | 55 |
|  |  | 50 | 100 | 82 | 17 |
|  |  | 50 | 50 | 63 | 17 |
|  |  | 50 | 12.5 | 57 | 17 |
|  |  | 25 | 50 | 39 | 0 |
|  |  | 25 | 25 | 35 | 0 |
|  |  | 12.5 | 25 | 30 | 0 |
| 7 | CPC-II/Bromophosethyl | 100 | 200 | 97 | 60 |
|  |  | 100 | 100 | 92 | 55 |
|  |  | 100 | 50 | 97 | 55 |
|  |  | 100 | 25 | 90 | 55 |
|  |  | 50 | 100 | 76 | 17 |
|  |  | 50 | 50 | 49 | 17 |
|  |  | 50 | 25 | 87 | 17 |
|  |  | 50 | 12.5 | 47 | 17 |
|  |  | 25 | 50 | 17 | 0 |
|  |  | 25 | 25 | 39 | 0 |
|  |  | 25 | 12.5 | 17 | 0 |
|  |  | 25 | 6.25 | 31 | 0 |
|  |  | 12.5 | 25 | 10 | 0 |
|  |  | 12.5 | 12.5 | 16 | 0 |
|  |  | 12.5 | 6.25 | 10 | 0 |

TABLE VII

| Example No | Cyclopropanecarboxylate, organophosphorus compound | Concentration ppm CPC-II | Concentration ppm OP | Mortality % Observed | Mortality % Expected |
|---|---|---|---|---|---|
| (Control) | CPC-II | 200 | — | 98 | — |
|  |  | 100 | — | 97 | — |
|  |  | 50 | — | 57 | — |
|  |  | 25 | — | 22 | — |
|  |  | 12.5 | — | 5 | — |
| (Control) | Chlorpyriphos | — | 200 | 0 | — |
| (Control) | Chlofenvinphos | — | 200 | 0 | — |
| (Control) | Fenthion-ethyl | — | 200 | 0 | — |
| (Control) | Diazinon | — | 200 | 0 | — |
| (Control) | Famphur | — | 200 | 0 | — |
| (Control) | Bromophosethyl | — | 200 | 0 | — |
| 8 | Chlorpyriphos/CPC-II | 100 | 200 | 98 | 97 |
|  |  | 50 | 100 | 100 | 57 |
|  |  | 25 | 50 | 90 | 22 |
|  |  | 12.5 | 25 | 70 | 5 |
| 9 | Chlorfenvinphos/CPC-II | 100 | 200 | 98 | 97 |
|  |  | 50 | 100 | 100 | 57 |
|  |  | 25 | 50 | 86 | 22 |
|  |  | 12.5 | 25 | 90 | 5 |
| 10 | Fenthionethyl/CPC-II | 100 | 200 | 100 | 97 |
|  |  | 50 | 100 | 98 | 57 |
|  |  | 25 | 50 | 96 | 22 |
|  |  | 12.5 | 25 | 80 | 5 |
| 11 | Diazinon/CPC-II | 100 | 200 | 100 | 97 |
|  |  | 50 | 100 | 98 | 57 |
|  |  | 25 | 50 | 98 | 22 |
|  |  | 12.5 | 25 | 74 | 5 |
| 12 | Famphur/CPC-II | 100 | 200 | 100 | 97 |
|  |  | 50 | 100 | 92 | 57 |
|  |  | 25 | 50 | 58 | 22 |
|  |  | 12.5 | 25 | 56 | 5 |
| 13 | Bromophosethyl/CPC-II | 100 | 200 | 100 | 97 |
|  |  | 100 | 100 | 100 | 97 |
|  |  | 100 | 50 | 100 | 97 |
|  |  | 50 | 100 | 98 | 57 |
|  |  | 50 | 50 | 100 | 57 |
|  |  | 50 | 25 | 100 | 57 |
|  |  | 25 | 50 | 78 | 22 |
|  |  | 25 | 25 | 98 | 22 |
|  |  | 25 | 12.5 | 82 | 22 |
|  |  | 12.5 | 12.5 | 90 | 5 |
|  |  | 12.5 | 6.25 | 70 | 5 |

I claim:

1. A composition of matter comprising as a tickicidally effective active ingredient a mixture comprising as a first component a compound selected from the group consisting of (a) (±)-α-cyano-3-phenoxybenzyl (±)-cis/trans-3-(2-chloro-3,3,3-trifluoro-prop-1-en-1-yl)-2,2-dimethylcyclopropane carboxylate (CPC-I) and (b) (±)-α-cyano-3-phenoxybenzyl (±)-cis-3-(2-chloro-3,3,3-trifluoroprop-1-en-1-yl)-2,2-dimethylcyclopropane carboxylate (CPC-II); and as a second component at least one insecticidal organophosphorus compound selected from the group consisting of cis/trans 2-chloro-1-(2,4-dichlorophenyl)-vinyl diethyl phosphate, O-(4-bromo-2,5-dichlorophenyl) O,O-diethyl phosphorothioate (bromophos-ethyl), O,O-diethyl O-(3,5,6-trichloro-2-pyridyl) phosphorothioate, and O,O,O',O'-tetraethyl-S,S'-methylene di(phosphorodithioate) (ethion), and wherein the weight ratio of the said first component to the said second component is in the range from 1:2 to 4:1 when the first component is CPC II and the second component is bromophos-ethyl or ethion and the said weight ratio is 1:2 for the remaining combinations.

2. A composition according to claim 1 wherein the said first component comprises a cis/trans isomer mixture of (±)-α-cyano-3-phenoxybenzyl (±)-3-(2-chloro-3,3,3-trifluoroprop-1-en-1-yl)-2,2-dimethylcyclopropane carboxylate.

3. A composition according to claim 1 wherein the said mixture constitutes up to 1% w/w of said composition.

4. A composition according to claim 3 wherein said mixture constitutes from 0.005 to 0.3% w/w of said composition.

5. A process for killing undesired *Boophilus microplus* (cattle tick) which process comprises treating media infested with *Boophilus microplus* with a tickicidally effective amount of the composition of claim 1.

6. A process according to claim 5 wherein said first component comprises a cis, trans isomer mixture of (±)-α-cyano-3-phenoxybenzyl (±)-3-(2-chloro-3,3,3-trifluoroprop-1-en-1-yl)-2,2-dimethylcyclopropane carboxylate.

7. A process according to claim 5 wherein the said first component comprises (±)-α-cyano-3-phenoxybenzyl (±)-cis-3-(2-chloro-3,3,3-trifluoroprop-1-en-1-yl)-2,2-dimethylcyclopropane carboxylate.

8. A process according to claim 5 wherein said cattle tick is of a non-resistant strain.

9. A process according to claim 5 wherein said cattle tick is of a resistant strain.

10. A composition according to claim 1 wherein the said first component comprises (±)-α-cyano-3-phenoxybenzyl (±)-cis-3-(2-chloro-3,3,3-trifluoroprop-1-en-1-yl)-2,2-dimethylcyclopropane carboxylate.

* * * * *